US009658445B2

(12) United States Patent
Yamamoto et al.

(10) Patent No.: US 9,658,445 B2
(45) Date of Patent: May 23, 2017

(54) ENDOSCOPE APPARATUS

(75) Inventors: Akihiro Yamamoto, Tokyo (JP);
Kiyotaka Shioiri, Hachioji (JP);
Mitsunobu Ono, Tokyo (JP);
Nobuyuki Motoki, Hachioji (JP)

(73) Assignee: OLYMPUS CORPORATION (JP)

( * ) Notice: Subject to any disclaimer, the term of this patent is extended or adjusted under 35 U.S.C. 154(b) by 454 days.

(21) Appl. No.: 13/416,220

(22) Filed: Mar. 9, 2012

(65) Prior Publication Data

US 2012/0226099 A1 Sep. 6, 2012

Related U.S. Application Data

(63) Continuation of application No. PCT/JP2009/065769, filed on Sep. 9, 2009.

(51) Int. Cl.
*A61B 1/00* (2006.01)
*A61B 1/04* (2006.01)
(Continued)

(52) U.S. Cl.
CPC ...... *G02B 23/2476* (2013.01); *A61B 1/00048* (2013.01); *A61B 1/00052* (2013.01);
(Continued)

(58) Field of Classification Search
CPC ............ A61B 1/00045; A61B 1/00048; A61B 1/00052; A61B 1/00112; A61B 1/00121; A61B 1/00124; A61B 1/0014
(Continued)

(56) References Cited

U.S. PATENT DOCUMENTS 6,221,007 B1 * 4/2001 Green ............... A61B 1/00052
600/104
6,951,537 B2 10/2005 Hirata ........................ 600/152
(Continued)

FOREIGN PATENT DOCUMENTS

JP 61-075315 4/1986
JP 03148618 A * 6/1991 ............... A61B 1/00
(Continued)

OTHER PUBLICATIONS

International Search Report mailed Nov. 17, 2009 in corresponding PCT International Application No. PCT/JP2009/065769.
(Continued)

*Primary Examiner* — Ryan Henderson
(74) *Attorney, Agent, or Firm* — Ostrolenk Faber LLP

(57) ABSTRACT

An endoscope apparatus includes: an endoscope including at least an elongated insertion section having flexibility and an image pickup device, the insertion section including, at a distal end portion, an observation window forming an observation optical system and an illumination window forming an illumination optical system and the image pickup device including an image pickup surface on which an optical image passing through the observation window is formed; and an apparatus body incorporating a display section that displays an image picked up by the image pickup device, the apparatus body including the display section on one surface having a largest area of the apparatus body and including a holding member that holds the insertion section on a rear surface of the one surface in a wound state.

5 Claims, 19 Drawing Sheets

(51) Int. Cl.
*A61B 1/06* (2006.01)
*G02B 23/24* (2006.01)
*A61B 1/05* (2006.01)
*A61B 1/005* (2006.01)

(52) U.S. Cl.
CPC ...... *A61B 1/00066* (2013.01); *A61B 1/00108* (2013.01); *A61B 1/005* (2013.01); *A61B 1/05* (2013.01)

(58) Field of Classification Search
USPC ........ 600/109–113, 160–181, 102, 104, 106, 600/107, 131; 356/241.1–241.6; 348/65–76
See application file for complete search history.

(56) References Cited

U.S. PATENT DOCUMENTS

| | | | | |
|---|---|---|---|---|
| 2003/0023142 A1* | 1/2003 | Grabover | ........... | A61B 1/00071 600/143 |
| 2004/0242958 A1 | 12/2004 | Fujikawa | ...................... | 600/102 |
| 2005/0085690 A1 | 4/2005 | Tien | ............................... | 600/109 |
| 2006/0215013 A1* | 9/2006 | Jongsma et al. | ........... | 348/14.08 |
| 2007/0038020 A1 | 2/2007 | Tien | ............................... | 600/101 |
| 2007/0070340 A1 | 3/2007 | Karpen | ...................... | 356/241.1 |
| 2008/0208002 A1 | 8/2008 | Maruyama | ................... | 600/131 |

FOREIGN PATENT DOCUMENTS

| | | |
|---|---|---|
| JP | 2004-086207 | 3/2004 |
| JP | 2004-321243 | 11/2004 |
| JP | 2005-118538 | 5/2005 |
| JP | 2005-270468 | 10/2005 |

OTHER PUBLICATIONS

Search Report issued by European Patent Office and received by applicant on Feb. 26, 2012 in connection with corresponding EP patent application No. EP 09 84 9196.

* cited by examiner

ENDOSCOPE APPARATUS

CROSS REFERENCE TO RELATED APPLICATION

This application is a continuation application of PCT/JP2009/065769 filed on Sep. 9, 2009, the entire contents of which are incorporated herein by this reference.

BACKGROUND OF THE INVENTION

1. Field of the Invention

The present invention relates to an endoscope apparatus that takes into account integrated carriage of an endoscope and an apparatus body.

2. Description of the Related Art

In a medical field and an industrial field, an endoscope having an elongated insertion section is widely used. Endoscopes used in the industrial field are used in airplane maintenance facilities, various kinds of factories, disaster-stricken areas, or the like.

For example, Japanese Patent Application Laid-Open Publication No. 2004-86207 (hereinafter referred to as Patent Literature 1) discloses an endoscope apparatus with which an endoscope apparatus body can be easily carried and breakage and the like of an insertion section is prevented even when the insertion section is removed to an outside of a case.

In this endoscope apparatus, in FIG. 18 and the like of Patent Literature 1, a configuration is shown in which an insertion section, an operation section, and a universal cable of a scope unit can be stored while being wound around plural protruding portions provided on one side surface of an endoscope body and being bound in a ring-like rounded shape.

In the endoscope apparatus disclosed in Patent Literature 1, as shown in FIGS. 20A to 20C, for example, a worker can carry the endoscope apparatus while holding an empty endoscope storage case or the endoscope body with one hand and slinging the endoscope body including a scope body, the endoscope body including the storage case, or a storage case for storing the scope unit over a shoulder on an opposite side.

In recent years, improvement of carriability has been desired in industrial endoscopes. Therefore, there are demands for a reduction in size and a reduction in weight of an apparatus and compacting of the entire apparatus.

Japanese Patent Application Laid-Open Publication No. 2004-321243 (hereinafter referred to as Patent Literature 2) discloses an endoscope apparatus in which an operation section is easily mounted on a housing section of an apparatus body.

In this endoscope apparatus disclosed in Patent Literature 2, in FIG. 2 and the like, a configuration is shown in which a mounting section for making it possible to detachably attach the operation section is provided on a side portion of the housing of the apparatus body. The mounting section includes a housing side mounting section provided on a side portion of the housing of the apparatus body and an operation section side mounting section provided on a side portion of the operation section of the endoscope. In the housing, fittings for belt attachment to which fittings of a belt are detachably connected are provided.

As a result, in the endoscope apparatus configured in this way, as shown in FIG. 1, an operator 6 can easily carry, by slinging a belt 3 provided in an apparatus body 2, to which an endoscope 1 is attached, over one shoulder, the endoscope apparatus while wearing the apparatus body 2 and the endoscope 1. In this carrying state, an insertion section 5 is wound around an operation section 4 attached to a side portion of the apparatus body 2 of the endoscope 1.

SUMMARY OF THE INVENTION

An endoscope apparatus according to one aspect of the present invention includes: an endoscope including at least an elongated insertion section having flexibility and an image pickup device, the insertion section including, at a distal end portion, an observation window forming an observation optical system and an illumination window forming an illumination optical system and the image pickup device including an image pickup surface on which an optical image passing through the observation window is formed; and an apparatus body incorporating a display section that displays an image picked up by the image pickup device, the apparatus body including the display section on one surface having a largest area of the apparatus body and including a holding member that holds the insertion section on a rear surface of the one surface in a wound state.

BRIEF DESCRIPTION OF THE DRAWINGS

FIGS. 2 to 12 are diagrams related to a first embodiment of the present invention, and FIG. 2 is a diagram for explaining an endoscope apparatus including an endoscope and an apparatus body according to the first embodiment of the present invention;

FIG. 3 is a diagram for explaining a hanger provided in an operation section;

FIG. 4 is a diagram for explaining a body attaching and detaching section and a stopper section provided in the apparatus body;

FIG. 6 is a diagram for explaining a body attaching and detaching section and a stopper section provided on a holding surface of the apparatus body;

FIG. 7 is a diagram for explaining a procedure for attaching the operation section to the apparatus body;

FIG. 8 is a diagram for explaining a regulating section formed between the operation section of the endoscope and the holding surface of the apparatus body and explaining a wound-state insertion section arranged in the regulating section;

FIG. 9 is a diagram of the endoscope apparatus in FIG. 8 viewed from an extending direction side of the insertion section extending from the operation section;

FIG. 10 is a diagram showing a state in which an operator is carrying, while slinging a belt over a shoulder, the endoscope apparatus including the operation section integral with the apparatus body;

FIG. 11 is a diagram for explaining a modification of the endoscope apparatus;

FIG. 12 is a diagram for explaining another modification of the endoscope apparatus and the like;

FIG. 14 is a side view of the endoscope apparatus in FIG. 13;

FIG. 15 is a diagram of the endoscope apparatus in FIG. 14 viewed from an arrow Y 15 direction and is a top view of the endoscope apparatus;

FIG. 16 is a diagram showing an insertion section integrally held on a holding surface side of the apparatus body;

FIG. 19 is a diagram showing the apparatus body including the grip, attaching sections of which are fixedly set on a left side surface section and a right side surface section of the apparatus body;

FIG. 20 is a diagram showing the apparatus body including a grip, attaching sections of which are fixedly set on an upper side surface section of the apparatus body;

FIG. 21 is a diagram showing the apparatus body including a grip, attaching sections of which are fixedly set on the holding surface of the apparatus body;

DETAILED DESCRIPTION OF THE PREFERRED EMBODIMENTS

Embodiments of the present invention are explained below with reference to the drawings.

A first embodiment of the present invention is explained with reference to FIGS. 2 to 10.

Figure 1:
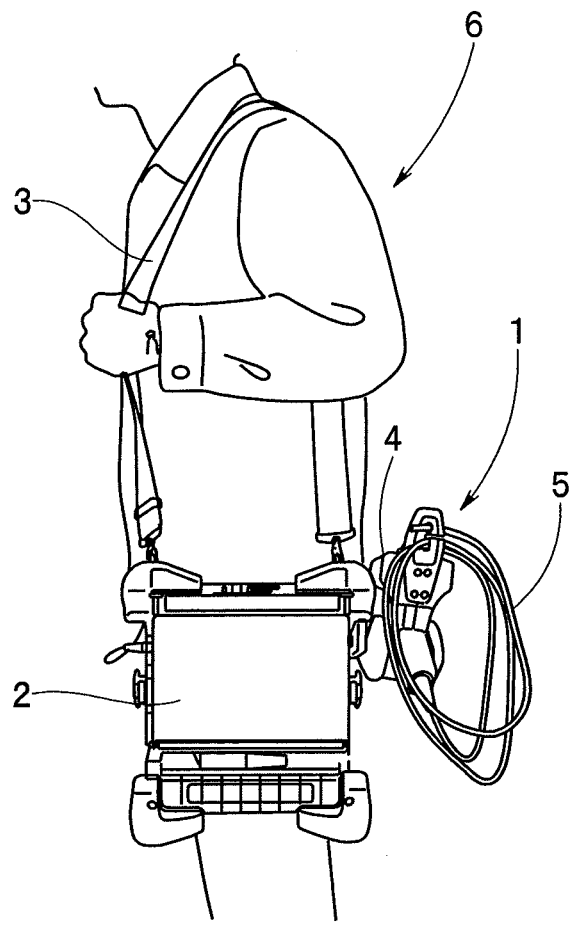
FIG. 1 is a diagram showing a carrying state of an endoscope apparatus in a state in which an operation section is attached to a side portion of an apparatus body.
Figure 2:
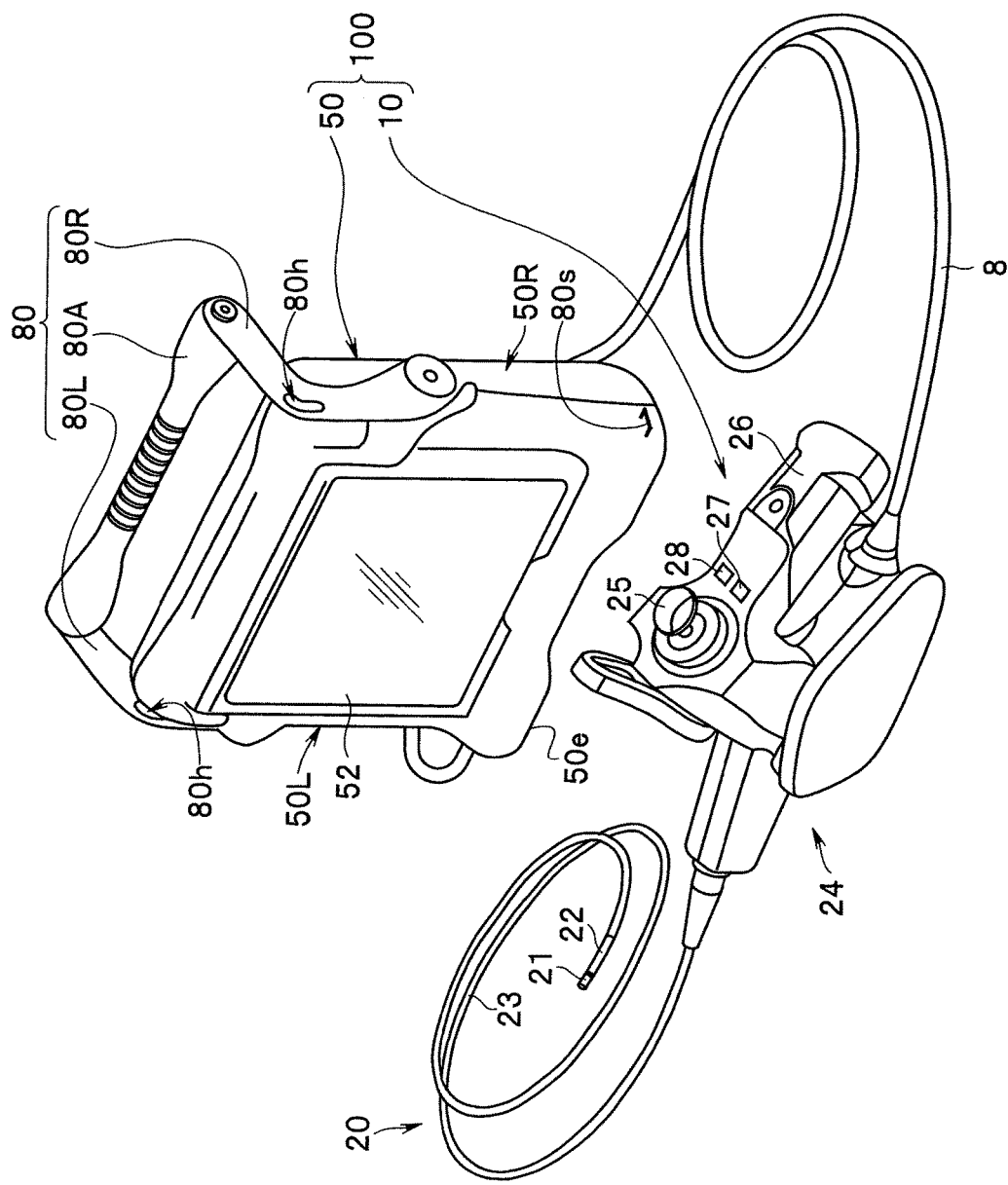

As shown in FIG. 2, an endoscope apparatus 100 according to the present embodiment includes an endoscope 10 and an apparatus body 50. The endoscope 10 includes an insertion section 20, an operation section 24, and a universal cable 8, which is an electric cable.

The insertion section 20 includes a hard distal end portion 21, a bendable bending portion 22, and a flexible tube portion 23. The insertion section 20 is inserted into, for example, an engine. The bending portion 22 is configured by joining plural bending pieces (not shown) to bend, for example, up and down and to the left and right.

A light emitting device (not shown) that emits illumination light and an image pickup device (not shown) such as a CCD or a C-MOS that forms an optical image passing through a not-shown observation window and converts the optical image into an electric signal are provided, for example, at the distal end portion of the insertion section 20. A distal end adapter including a light emitting device and an optical lens forming an observation optical system may be detachably attached to the distal end portion 21.

In the operation section 24, a bending operation lever 25 standing upright with respect to a top surface is provided.

The bending operation lever 25 is configured to be tiltably operable at least in four directions. The bending portion 21, by appropriately changing a tilting direction and a tilting angle of the lever 25, performs a bending action according to the tilting direction and the tilting angle.

A proximal end portion of the insertion section 20 is coupled to the operation section 24. The universal cable 8 is extended from the operation section 24 and coupled to, for example, a left side surface section 50L of the apparatus body 50.

Reference numeral 26 denotes a grasping section grasped by an operator. Reference numeral 27 denotes an image immobilizing switch. The image immobilizing switch 27 performs an instruction for immobilizing an endoscope image displayed on a display section explained later. Reference numeral 28 denotes an image recording switch. The image recording switch 28 instructs recording of an endoscope image displayed on the display section explained later.

In the apparatus body 50, a display section 52 is provided on a principal plane 51, which is one of surfaces having a largest area. For example, an endoscope image, which is an image picked up by the image pickup device, is displayed on the display section 52. The apparatus body 50 includes, on an inside thereof, an electric circuit that performs driving of the image pickup device, a signal processing section including an image processing circuit or the like that generates a video signal from an image signal outputted from an image pickup unit and outputs the video signal to the display section, a recording section that records image data processed by the image processing circuit, a light source section including a light adjustment circuit or the like that controls an illumination light amount, and a battery or the like functioning as a power supply section that supplies necessary electric power into the endoscope and the apparatus body.

The apparatus body 50 according to this embodiment has a flat rectangular parallelepiped shape. A grip 80 that improves portability and enables the apparatus body 50 to be used upright is provided in the apparatus body 50.

The grip 80 includes a grasping bar 80A and a pair of arm sections 80R and 80L having a substantially L shape. One end of the right side arm section 80R is pivotably attached to a right side surface section 50R. One end of the left side arm section 80L is pivotably attached to the left side surface section 50L. The other end of the right side arm section 80R and the other end of the left side arm section 80L are respectively fixedly set on one end face and the other end face of the grasping bar 80A.

Reference numeral 80h denotes belt attachment holes. The belt attachment holes 80h are provided in bent portions of the arm sections 80L and 80R. Hooks included in a belt (reference numeral 81 in FIG. 10) can be attached to the belt attachment holes 80h. Reference numeral 80s denotes belt attachment fittings. The belt attachment fittings 80s are provided, for example, on setting surface sides of the side surface sections 50L and 50R. The hooks included in the belt can also be attached to the belt attachment fittings 80s.

The left side surface section 50L indicates a left side surface at the time when the principal plane 51 is viewed from the front. A right side surface indicates a surface on an opposite side of the left side surface.

A signal line connected to the image pickup device and a power supply line for supplying electric power to the light emitting device are inserted through the insertion section 20. In addition to the signal line and the power supply line, a power supply line for motor for supplying electric power to a not-shown driving motor provided in the operation section 24 is inserted through the universal cable 8.

The endoscope apparatus 100 according to the present embodiment includes an attaching and detaching mechanism section that integrates the endoscope 10 and the apparatus body 50 taking carriability into account.

Figure 3:
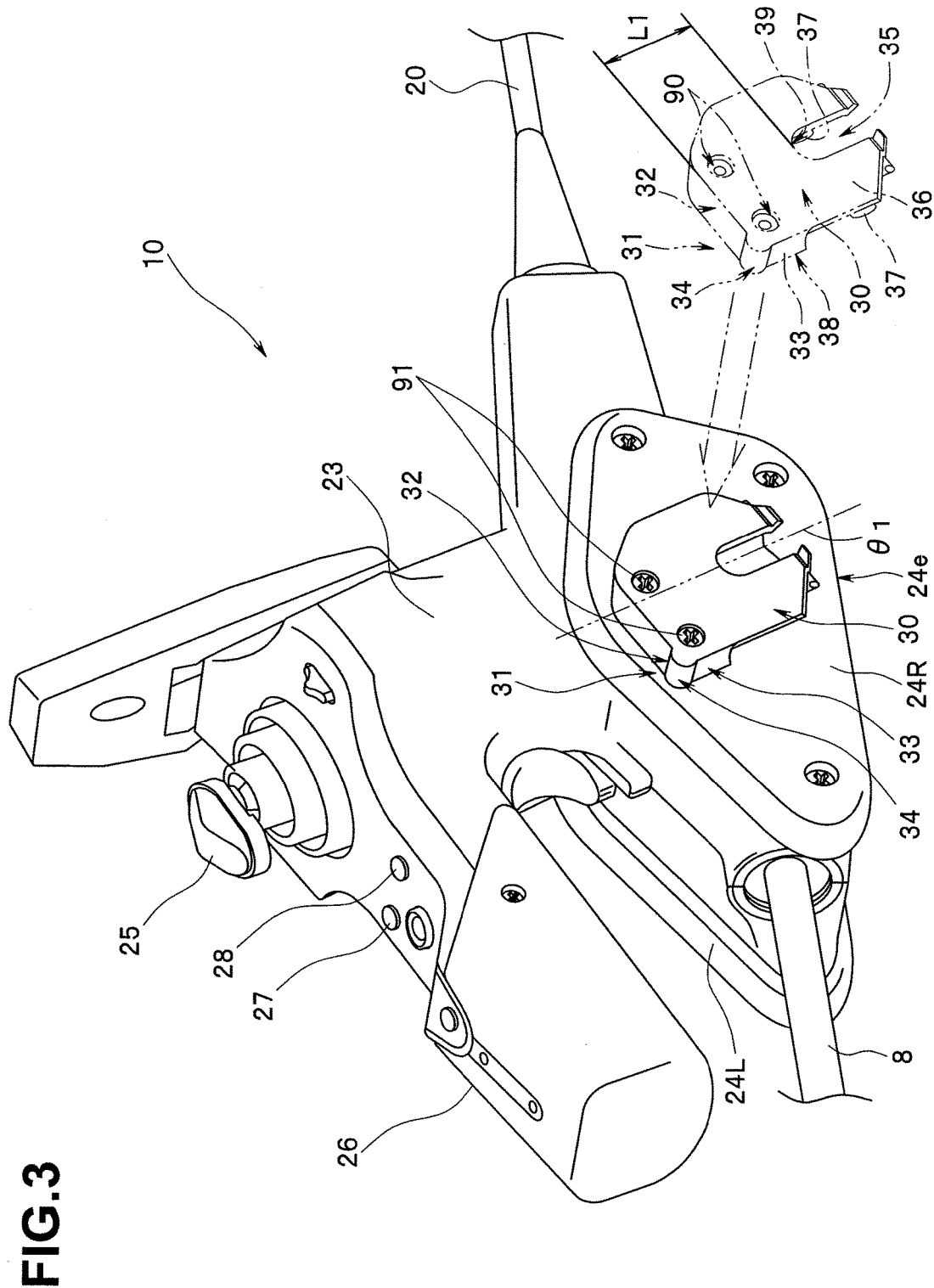

As shown in FIG. 3, a hanger 30 is provided as an operation section side attaching and detaching section on a side surface of, for example, a right leg section 24R, which is one of a leg section 24L and a leg section 24R of the operation section 24 included in the endoscope 10. The hanger 30 is a first attaching and detaching section of the attaching and detaching mechanism section.

Figure 4:
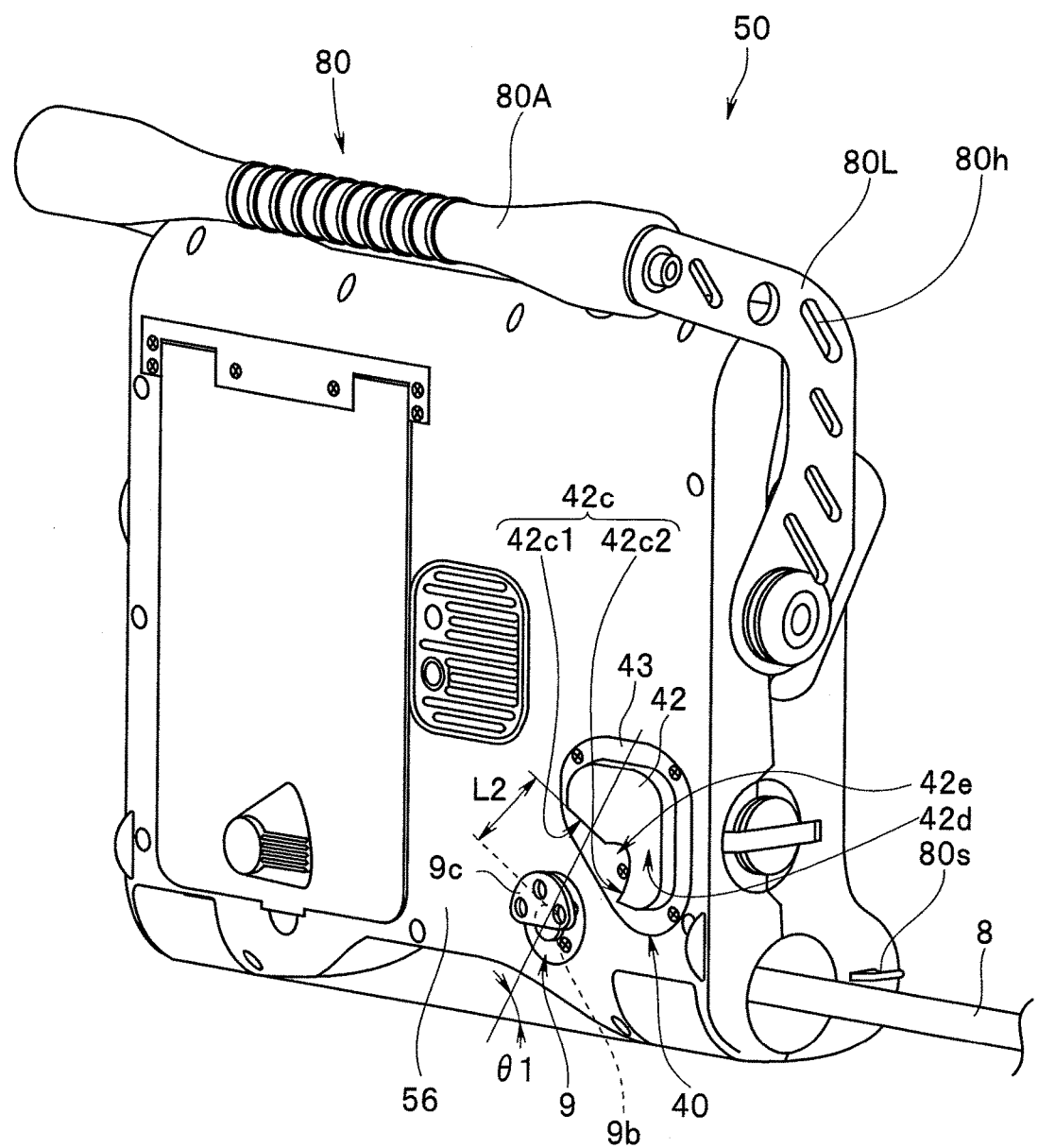

On the other hand, a body attaching and detaching section 9, to which the hanger 30 is detachably attached, is provided as an apparatus body side attaching and detaching section on a holding surface 56 shown in FIG. 4, which is a rear surface of the principal plane 51 including the display section 52. The body attaching and detaching section 9 is a second attaching and detaching section of the attaching and detaching mechanism section. Reference numeral 40 denotes a stopper section functioning as an operation and holding section that functions as both a fall-off preventing section and a switching operation section.

The hanger 30 indicated by an alternate long and two short dashes line in FIG. 3 is formed of, for example, a hard resin member. The hanger 30 includes a protruding section 36 and a fixed section 38. The protruding section 36 includes a locking groove 35. The fixed section 38 includes a holding section 31 including, for example, holding surfaces 32 and 33 orthogonal to each other and a curved surface convex section 34.

A pair of bosses 37 are protrudingly provided on a rear surface side of the protruding section 36 across the locking groove 35. A distance from a terminal end 39 of the locking groove 35 to the holding surface 32 orthogonal to a center line of the locking groove 35 is set to a predetermined dimension L1 (hereinafter also referred to as distance L1).

The curved surface convex section 34 is formed in a crossing section of the holding surface 32 and the holding surface 33. Reference numeral 90 denotes a counter boring hole. The counter boring hole 90 is formed on a front surface side of the fixed section 38. A screw 91 is disposed in the counter boring hole 90.

The hanger 30 is fixed to a side surface of the right leg section 24R by screws 91 in a state in which a rear side surface of the fixed section 38 and rear side surfaces of the bosses 37 are set in contact with the side surface of the right leg section 24R. In this fixed state, the center line of the locking groove 35 included in the hanger 30 is tilted at a predetermined angle $\theta 1$ with respect to a setting surface 24e, which is a bottom surface of the right leg section 24R.

As shown in FIG. 4, the body attaching and detaching section 9 and the stopper section 40 are arrayed taking into account the distance L1 from the terminal end 39 to the holding surface 32 and the angle $\theta 1$.

Figure 5A:
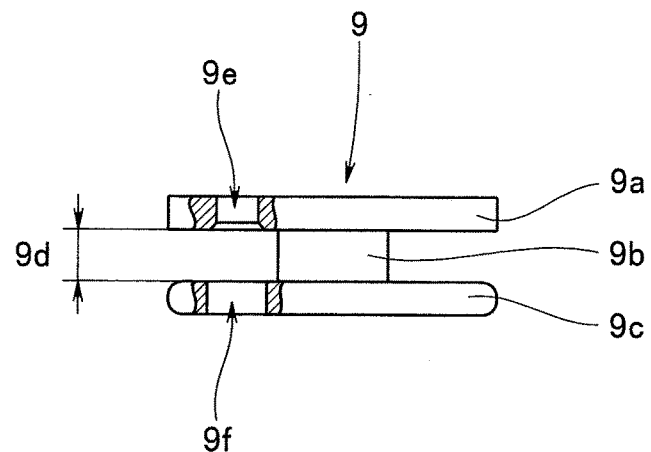
FIG. 5A is a top view for explaining a configuration of the body attaching and detaching section.
Figure 5B:
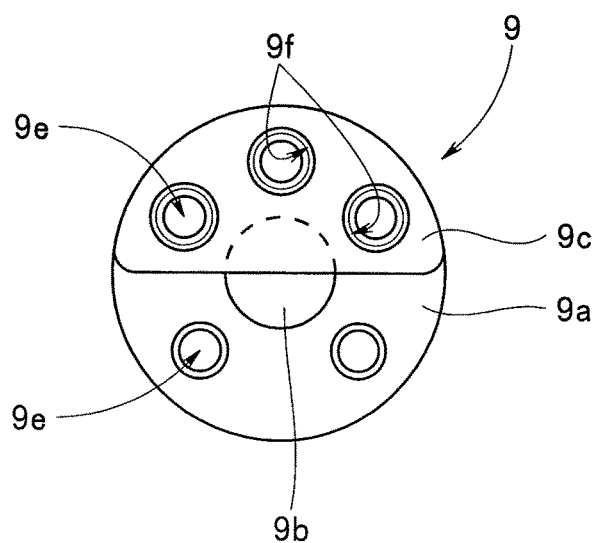
FIG. 5B is a front view for explaining the configuration of the body attaching and detaching section.
Figure 6:
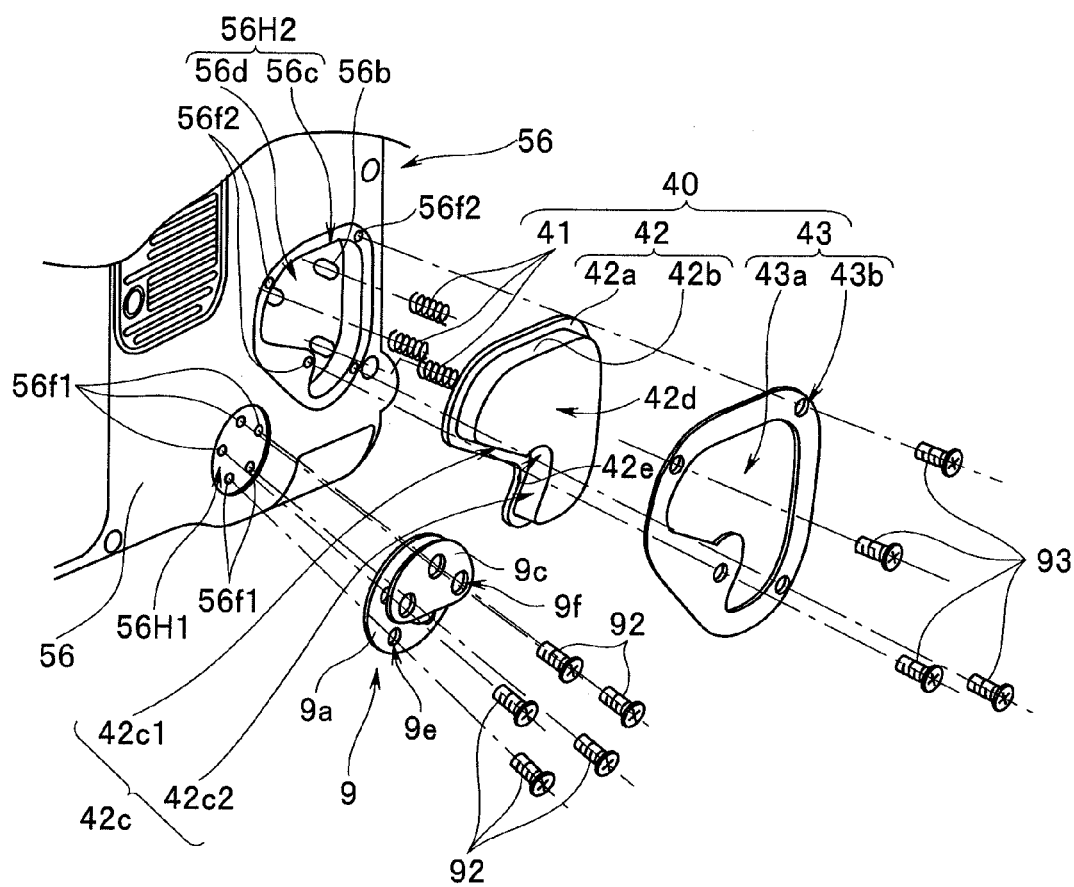

The body attaching and detaching section 9 is a hanger locking section and is made of metal such as stainless steel. As shown in FIGS. 5A, 5B, and 6, the body attaching and detaching section 9 includes a fixed circular plate section 9a, a supporting column 9b vertically provided from a center of the fixed circular plate section 9a, and a holding section 9c opposed to the fixed circular plate section 9a across the supporting column 9b.

A diameter dimension of the supporting column 9b is set taking into account a width dimension of the locking groove 35 of the hanger 30 and set smaller than the width dimension of the locking groove 35 by a predetermined dimension. A gap 9d between the fixed circular plate section 9a and the holding section 9c is set taking into account a thickness dimension of the protruding section 36 of the hanger 30 and set larger than the thickness dimension of the protruding section 36 by a predetermined dimension.

Consequently, after an opening of the locking groove 35 of the hanger 30 is set opposed to the supporting column 9b of the body attaching and detaching section 9, the hanger 30 is brought closer to the body attaching and detaching section 9, whereby the supporting column 9b of the body attaching and detaching section 9 is arranged in the locking groove 35 of the hanger 30 and the protruding section 36 of the hanger 30 is disposed in the gap 9d of the body attaching and detaching section 9. The hanger 30 is hooked to the body attaching and detaching section 9, i.e., locked.

For example, five screw arrangement holes 9e, in which screws 92 are arranged, are formed in the fixed circular plate section 9a. On the other hand, for example, three screw through-holes 9f, through which the screws 92 are inserted, are formed in the holding section 9c. The fixed circular plate section 9a of the body attaching and detaching section 9 is arranged in a first concave section 56H1 formed on the holding surface 56 as shown in FIG. 6.

A depth dimension of the first concave section 56H1 is set substantially the same as a thickness dimension of the fixed circular plate section 9a. Female screw sections 56f1 are formed to correspond to the screw arrangement holes 9e on a bottom surface of the first concave section 56H1. After the fixed circular plate section 9a is arranged in a predetermined direction in the first concave section 56H1, the body attaching and detaching section 9 is integrally fixed on the holding surface 56 by the screws 92 as shown in FIG. 4.

As shown in FIG. 6, the stopper section 40 includes, for example, three coil springs 41 functioning as urging members, a stopper 42, and a stopper regulating plate 43.

On the holding surface 56, a second concave section 56H2 for providing the stopper section 40 is formed. The second concave section 56H2 includes a regulating plate fixing stepped section 56c and a stopper disposing hole 56d. A depth dimension from the holding surface 56 to a bottom surface of the second concave section 56H2 is set substantially the same as a thickness dimension of the stopper 42. The stopper disposing hole 56d is formed such that a regulating section explained later is opposed to the body attaching and detaching section 9 in a state in which the stopper 42 is arranged in the hole.

Three protrusions 56b are integrally provided on the bottom surface of the second concave section 56H2, i.e., a bottom surface of the stopper disposing hole 56d. A height dimension of the protrusions 56b is set to a predetermined dimension. The coil springs 41 projecting more than the protrusions 56b by a predetermined amount are arranged on the protrusions 56b. The coil springs 41 are compression springs and press the stopper 42 to project from the holding surface 56.

The regulating plate fixing stepped section 56c is formed to surround the stopper disposing hole 56d. A depth dimension from the holding surface 56 to a bottom surface of the regulating plate fixing stepped section 56c is set substantially the same as a thickness dimension of the stopper regulating plate 43. For example, four female screw sections 56f2 are formed on the bottom surface of the regulating plate fixing stepped section 56c.

The stopper 42 has a substantially convex shape as a sectional shape and is formed of a hard resin member or a metal member such as stainless steel. The stopper 42 includes an edge portion 42a and a stopper body 42b.

The stopper body 42b is vertically provided a predetermined height from the edge portion 42a. On a plane on the edge portion 42a side of the stopper body 42b, holes for springs (no shown) having a predetermined depth dimension, into which the coil springs 41 arranged on the protrusions 56b are inserted and arranged, are formed.

The edge portion 42a is slidably arranged in the stopper disposing hole 56d. The stopper body 42b includes a regulating section 42c functioning as a fall-off preventing section and a pressing surface 42d functioning as a switching operation section. The regulating section 42c includes contact surfaces 42c1 and 42c2 and an engaging section 42e.

The contact surfaces 42c 1 and 42c2 come into contact with the holding surfaces 32 and 33 of the holding section 31 of the hanger 30 and regulate the locking groove 35 from moving in a direction in which the locking groove 35 falls off from the supporting column 9b. The pressing surface 42d is an upper surface of the stopper body 42b and is pressed by the operator. The engaging section 42e is a recess provided in a crossing section of the contact surface 42c1 and the contact surface 42c2, the curved surface convex section 34 is arranged on the engaging section 42e.

The stopper regulating plate 43 is formed of a thin plate of metal such as stainless steel. In the stopper regulating plate 43, an opening 43a, from which the stopper body 42b is projected such that the edge portion 42a comes into contact with the stopper regulating plate 43, and, for example, four screw holes 43b, through which screws 93 are inserted and arranged, are formed. A shape of the opening 43a is set larger than an external shape of the stopper body 42b by a predetermined dimension. An external shape of the stopper regulating plate 43 is set smaller than the regulating plate fixing stepped section 56c by a predetermined dimension.

The edge portion 42a of the stopper body 42b comes into contact with the stopper regulating plate 43 fixed to the regulating plate fixing stepped section 56c. A distance L2 from the contact surface 42c1 of the stopper body 42b, the edge portion 42a of which comes into contact with the stopper regulating plate 43, protrudingly provided from the holding surface 56 to an outer circumference of the supporting column 9b is substantially the same dimension as the distance L1 shown in FIG. 3 and set longer than the distance L1 by a predetermined dimension.

The female screw sections 56f2 formed in the regulating plate fixing stepped section 56c is formed in positions corresponding to the screw holes 43b formed in the stopper regulating plate 43. The screws 93 are screwed into the female screw sections 56f2.

A procedure for disposing the stopper section 40 on the holding surface 56 is explained.

First, the worker arranges the coil springs 41 on the protrusions 56b in a state in which the holding surface 56 is faced upward. Subsequently, the worker inserts the distal end portion of the coil springs 41 into the holes for springs formed in the stopper 42. Consequently, the stopper 42 is placed on the coil springs 41. Subsequently, the worker arranges the stopper regulating plate 43 on the edge portion 42a of the stopper 42. In this state, the operator inserts the stopper 42 into the stopper disposing hole 56d against urging force of the coil springs 41. The operator arranges the stopper regulating plate 43 in the regulating plate fixing stepped section 56c. The operator screws the four screws 93 into the female screw sections 56f2 via the screw holes 43b.

Consequently, as shown in FIG. 4, the stopper 42 included in the stopper section 40 is pushed up by the urging force of the coil springs 41 and disposed in a state in which the stopper 42 projects from the holding surface 56. The stopper 42 projecting from the holding surface 56 is pushed down by pressing the pressing surface 42d of the stopper body 42b against the urging force of the coil springs 41.

In other words, in the present embodiment, the stopper 42 freely projects and recedes and is set to change to a projecting state in which the pressing surface 42d projects a predetermined amount with respect to the holding surface 56 and a receding state in which the pressing surface 42d substantially flushes with the holding surface 56. The projecting state of the stopper 42 is a held state. The receding state of the stopper 42 is a detachably attachable state.

The distance L2 from the contact surface 42c1 of the stopper 42, which projects from the holding surface 56, to an outer circumference of the supporting column 9b is set longer than the distance L1 by a predetermined dimension. Therefore, when the hanger 30 is attached to the body attaching and detaching section 9 in a predetermined state, the endoscope 10 and the apparatus body 50 change to the held state in which the contact surfaces 42c1 and 42c2 of the stopper 42 projected by the urging force of the coil springs 41 are in contact with the holding surfaces 32 and 33 of the hanger 30. The hanger 30 locked to the body attaching and detaching section 9 is surely prevented from falling off.

An attaching procedure for disposing the hanger 30, which is provided in the operation section 24 of the endoscope 10, in the body attaching and detaching section 9 and the stopper section 40 of the apparatus body 50, changing the endoscope 10 and the apparatus body 50 to an integrally fixed state, and enabling the endoscope apparatus 100 to be carried is explained.

In integrally attaching the endoscope 10 and the apparatus body 50, the operator moves the grip 80 to the principal plane 51 side in advance.

Figure 7:
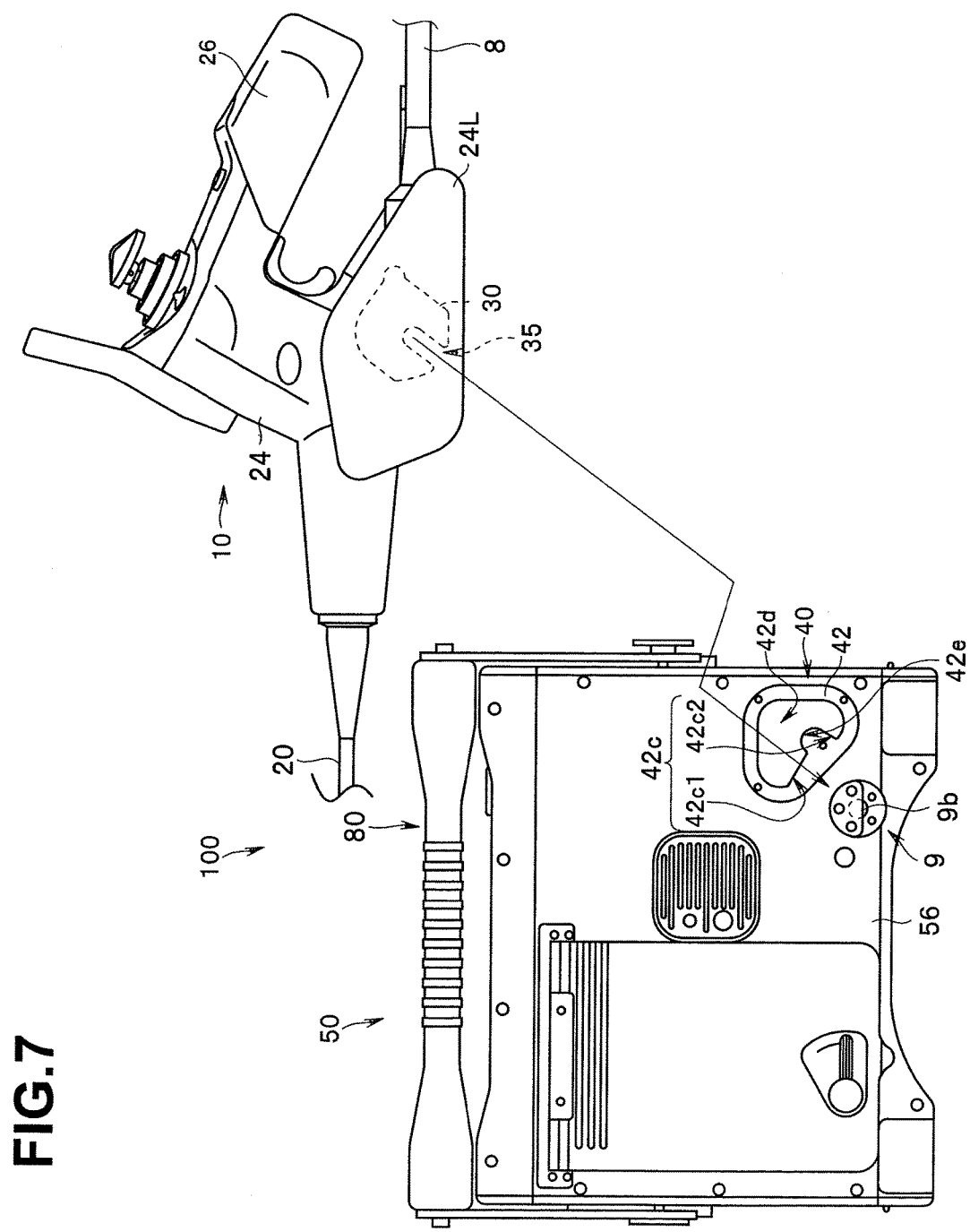

Thereafter, as shown in FIG. 7, the operator sets the locking groove 35 of the hanger 30 indicated by broken lines, which are provided in the right leg section 24R of the operation section 24 included in the endoscope 10, to be substantially opposed to the body attaching and detaching section 9 provided on the holding surface 56 included in the apparatus body 50.

The operator brings the hanger 30 closer toward the stopper section 40 spaced apart from the body attaching and detaching section 9. After confirming that a front side surface of the hanger 30 and a front side surface of the stopper section 40 move to positions where the front side surfaces are substantially opposed to each other, the operator moves the front side surface of the hanger 30 toward the front side surface of the stopper section 40.

The operator brings the front side surface of the protruding section 36 of the hanger 30 into contact with the pressing surface 42d of the stopper 42 of the stopper section 40, pushes down the stopper 42 projecting from the holding surface 56 against the urging force of the coil springs 41, and moves the opening of the locking groove 35 of the hanger 30 toward the supporting column 9b.

The operator performs alignment such that the supporting column 9b is arranged in the locking groove 35 and arranges the supporting column 9b in the locking groove 35. The operator moves the hanger 30 until the terminal end 39 of the locking groove 35 comes into contact with the supporting column 9b. The operator sets the hanger 30 in a predetermined locked state to the body attaching and detaching section 9.

Then, pressing force for pressing the pressing surface 42d of the stopper 42 by the hanger 30 is released and the stopper 42 of the stopper section 40 projects with the urging force of the coil springs 41.

Consequently, the contact surfaces 42c1 and 42c2 of the stopper 42 come into contact with the holding surfaces 32 and 33 of the hanger 30 while the curved surface convex section 34 is engaged and arranged in the engaging section 42e. The endoscope 10 and the apparatus body 50 changes to the held state in which the operation section 24 is regulated from rotating with respect to the holding surface 56 of the apparatus body 50 and falling off.

In this held state, the operation section 24 functions as a holding member 70.

Figure 8:
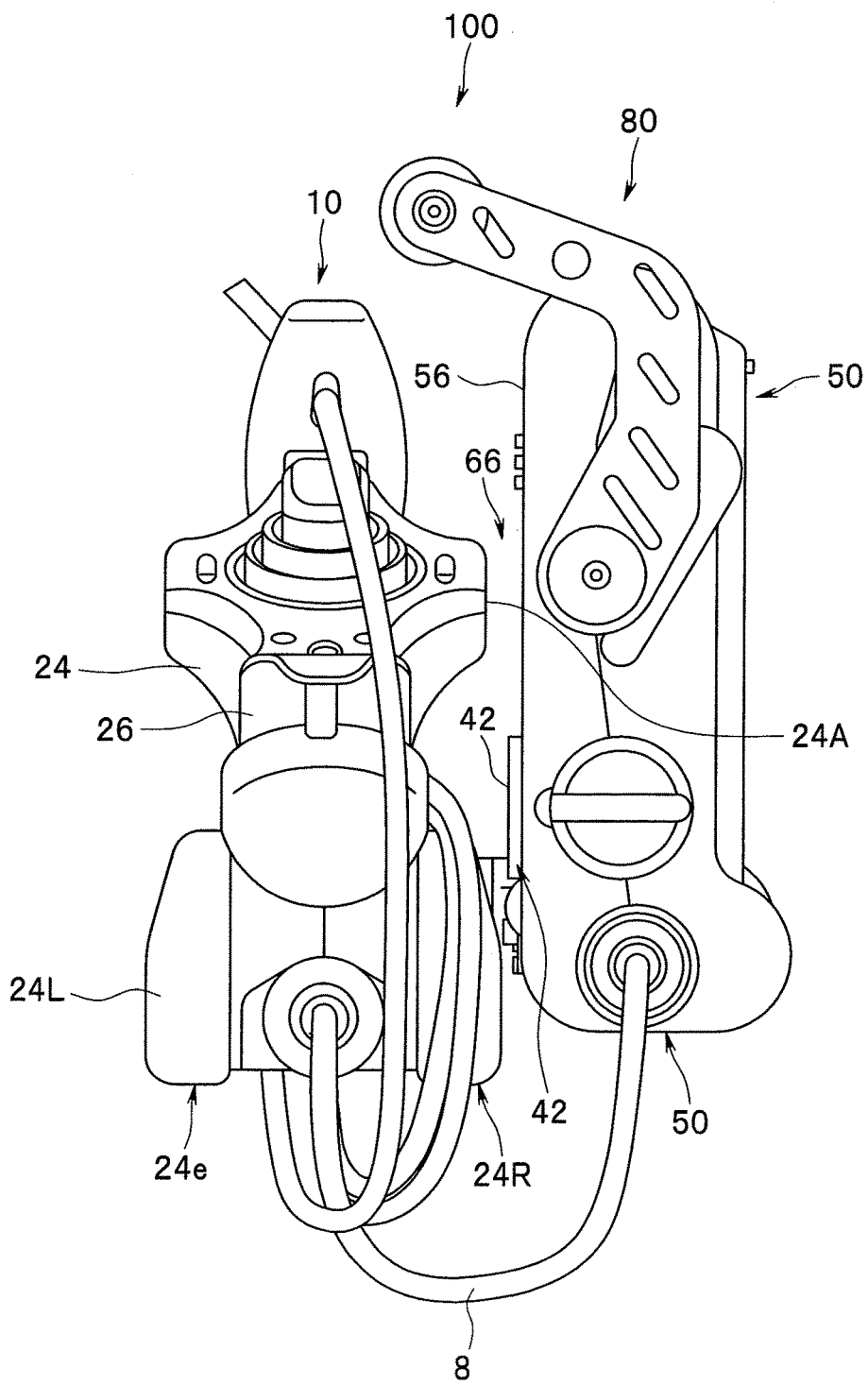

Specifically, as shown in FIG. 8, the body section 24A of the operation section 24 functions as a first regulating section that regulates the insertion section 20 from moving in an axial direction perpendicular to the holding surface 56, i.e., projecting. The right leg section 24R held by the holding surface 56 functions as a second regulating section that regulates the insertion section 20 from moving in a gravity direction.

Therefore, as shown in FIG. 8, the operator arranges the wound-state insertion section 20A, which is formed by winding the insertion section 20 extending from the operation section 24, on the right leg section 24R including the first regulating section and the second regulating section through a gap 66 between the operation section 24 and the holding surface 56.

The operator inserts the distal end portion 21 of the insertion section 20 through a pressing hole 29a formed in a protection plate 29 provided in the operation section 24. Consequently, the distal end portion 21 of the insertion section 20 is stably held.

Figure 9:
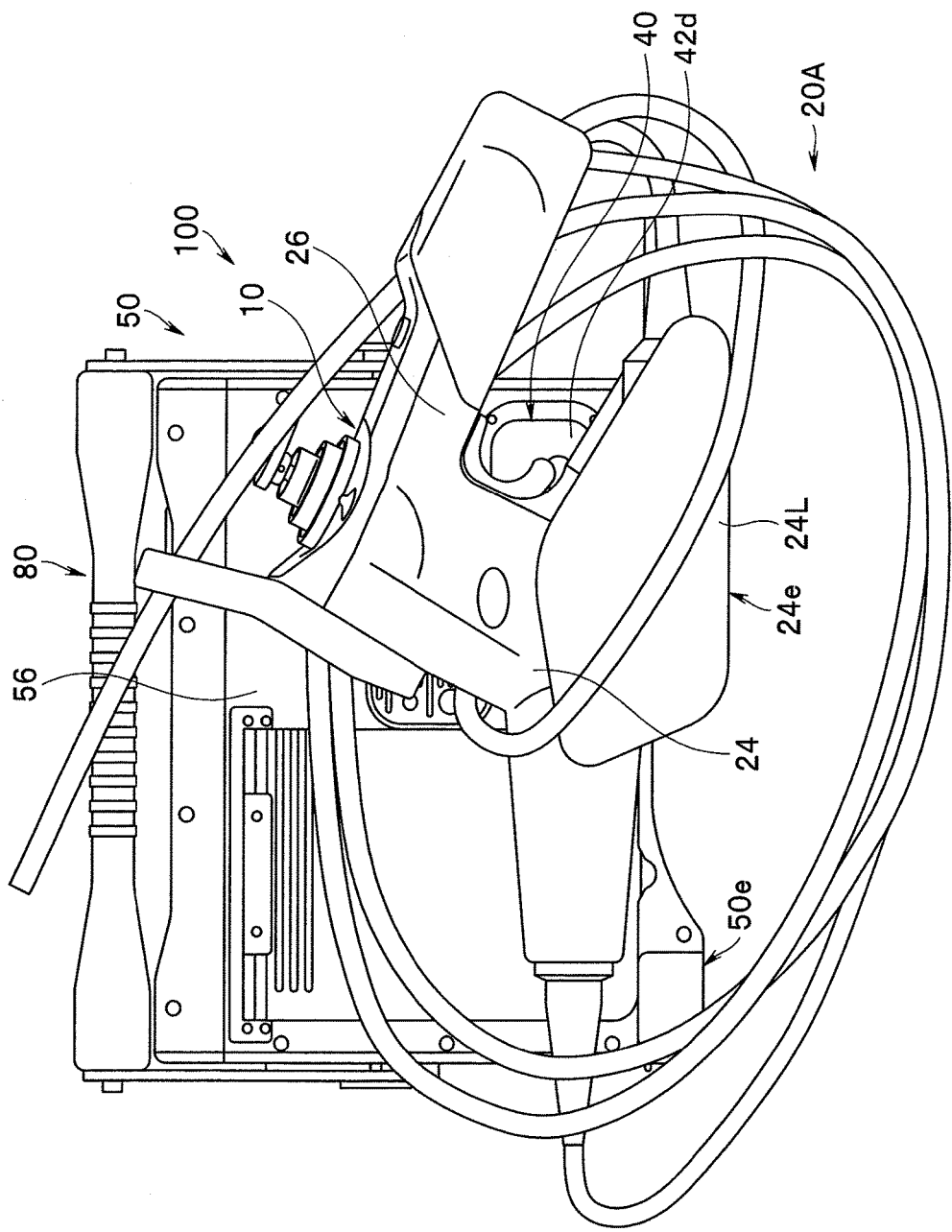

Consequently, as shown in FIGS. 8 and 9, an insertion section held state in which the wound-state insertion section 20 is compactly held between the operation section 24 and the apparatus body 50 can be obtained.

Figure 10:
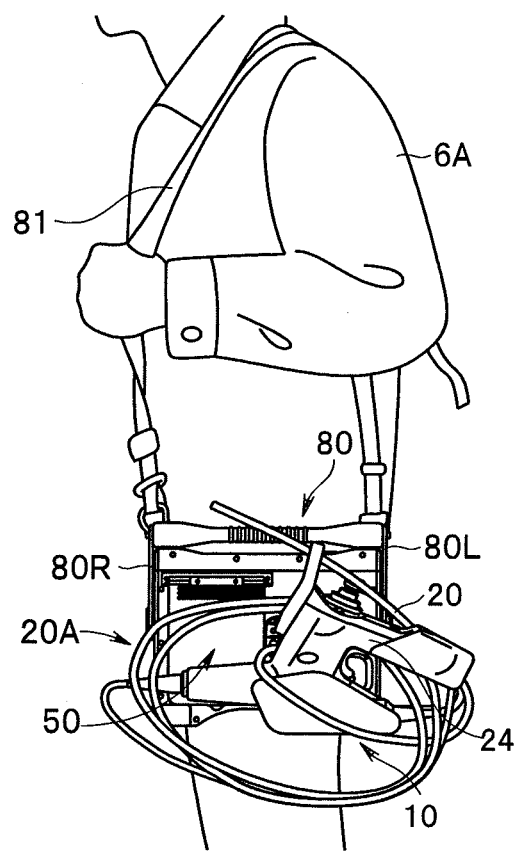

In this insertion section held state, the hooks of the belt 81 are respectively attached to the belt attachment holes 80h. Therefore, as shown in FIG. 10, the operator can wear the endoscope apparatus 100 in which the apparatus body 50 and the operation section 24 of the endoscope 10 are integrated and the wound-state insertion section 20A is held between the operation section 24 and the apparatus body 50.

In this state, the hanger 30 of the operation section 24 is locked to the body attaching and detaching section 9 of the holding surface 56. Further, the fixed section 38 of the locked hanger 30 is in contact with and held on the contact surfaces 42c1 and 42c2 of the stopper 42. Therefore, as shown in the figure, an operator 6A can hold the belt 81 and carry the endoscope apparatus 100 without touching the operation section 24.

A removal procedure for separating the endoscope 10 and the apparatus body 50 after the carrying is explained.

When the operator separates the operation section 24 integrally attached to the holding surface 56 of the apparatus body 50 from the endoscope 10, for example, the operator grasps the grasping section 26 and touches the pressing surface 42d of the stopper 42 with the gripping fingers. The operator presses the pressing surface 42d and pushes down the stopper 42, which projects from the holding surface 56, against the urging force of the coil springs 41.

Thereafter, the operator moves the hanger 30 attached to the body attaching and detaching section 9 in a direction of the stopper section 40. At this point, since the stopper 42 is pushed down, the front side surface of the hanger 30 is arranged on the pressing surface 42d of the stopper 42.

The operator moves the hanger 30 to separate from the body attaching and detaching section 9, whereby the locked state of the body attaching and detaching section 9 and the hanger 30 is released. The endoscope 10 and the apparatus body 50 change to the separated state again. This allows the operator to perform an observation. In other word, after carrying the endoscope apparatus 100, the operator can immediately shift to observation using the endoscope 10.

Figure 11:
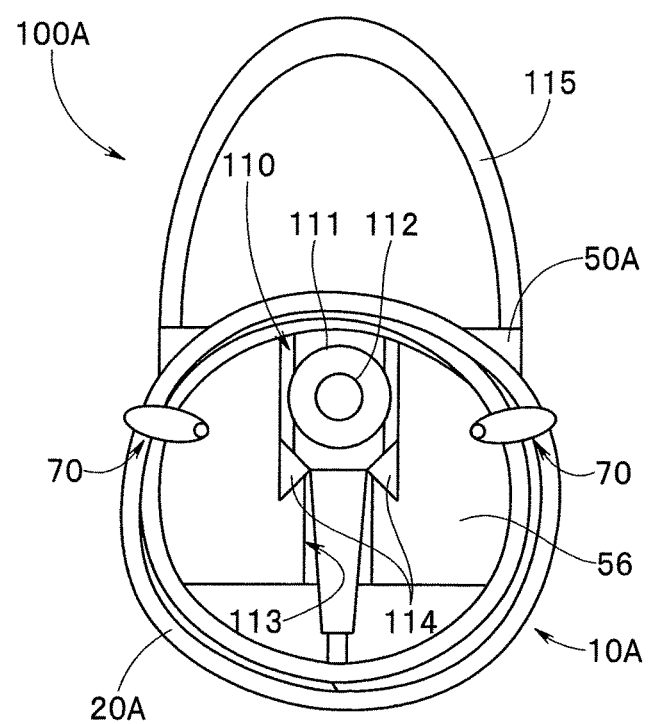

In the embodiment explained above, the bending operation lever 25 is included in the operation section 24 of the endoscope 10. However, the endoscope 10 is not limited to the configuration including the bending operation lever 25 for bending the bending section 22. As indicated by a modification shown in FIG. 11, the endoscope 10 may be an endoscope 10A including an operation section 110 including rotating knobs 111 and 112.

In this endoscope apparatus 100A, the operation section 110 included in the endoscope 10A is arranged in a groove 113 formed on the holding surface 56 of an apparatus body 50A. The operation section 110 is nipped by elastic members 114 and pressed and held in the groove 113. Reference numeral 115 denotes a belt.

In this way, in the endoscope 10A having the configuration in which the operation section 110 includes the rotating knobs 111 and 112, as in the endoscope 10, the groove 113 in which the operation section 110 is disposed and the elastic members 114 for fixedly setting the operation section 110 are provided in the apparatus body 50A. This makes it possible to integrally carry the endoscope 10A and the apparatus body 50A.

Figure 12:
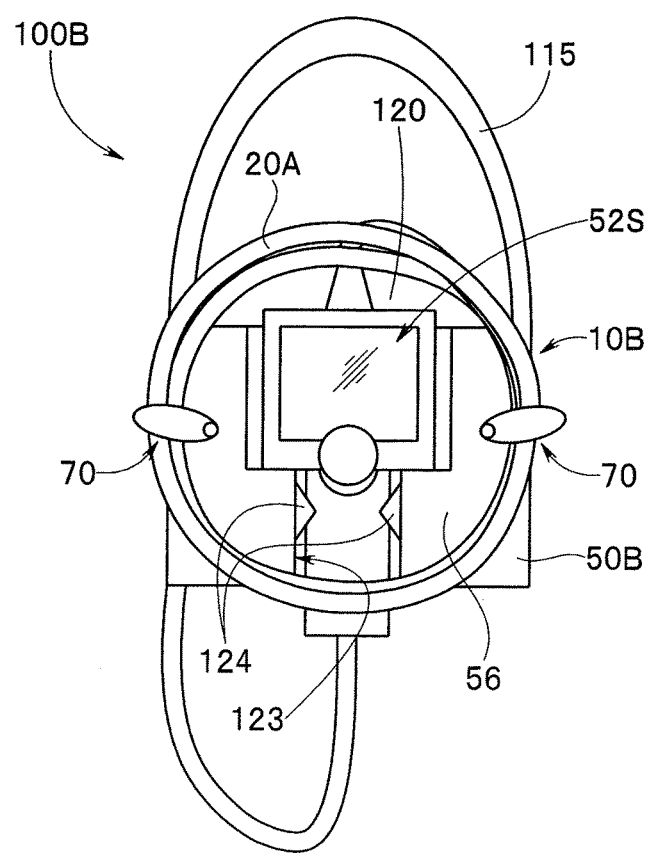

In the embodiment explained above, the display section 52 is provided on the principal plane 51 of the apparatus body 50. However, as indicated by another modification shown in FIG. 12, a display section 52S may also be provided in, for example, an operation section 120 of an endoscope 10B.

In this endoscope apparatus 100B, for example, a display section on the apparatus body 50B side is used as a main display section and the display section 52S on the operation section 120 side is exclusively used for an observation.

The main display section has, for example, a function of increasing a size of an endoscope image in order to make it easy to perform measurement and adopts a touch panel system. By adopting the touch panel system, it is possible to eliminate operation buttons from the principal plane 51.

In the endoscope apparatus 100B configured in this way, for example, an operation section 120 is integrally held on the apparatus body 50B. Specifically, the operation section 120 included in the endoscope 10B is arranged in a groove 123 formed in the apparatus body 50B. The operation section 120 is nipped by elastic members 124 and pressed and held in the groove 123.

In this way, in the endoscope 10B having the configuration in which the display section 52S is provided in the operation section 120, as in the endoscopes 10 and 10A, the groove 123 in which the operation section 120 is disposed and the elastic members 124 for fixedly setting the operation section 120 are provided in the apparatus body 50B. This makes it possible to integrally carry the endoscope 10B and the apparatus body 50B.

A second embodiment of the present invention is explained with reference to FIGS. 13 to 16.

Figure 13:
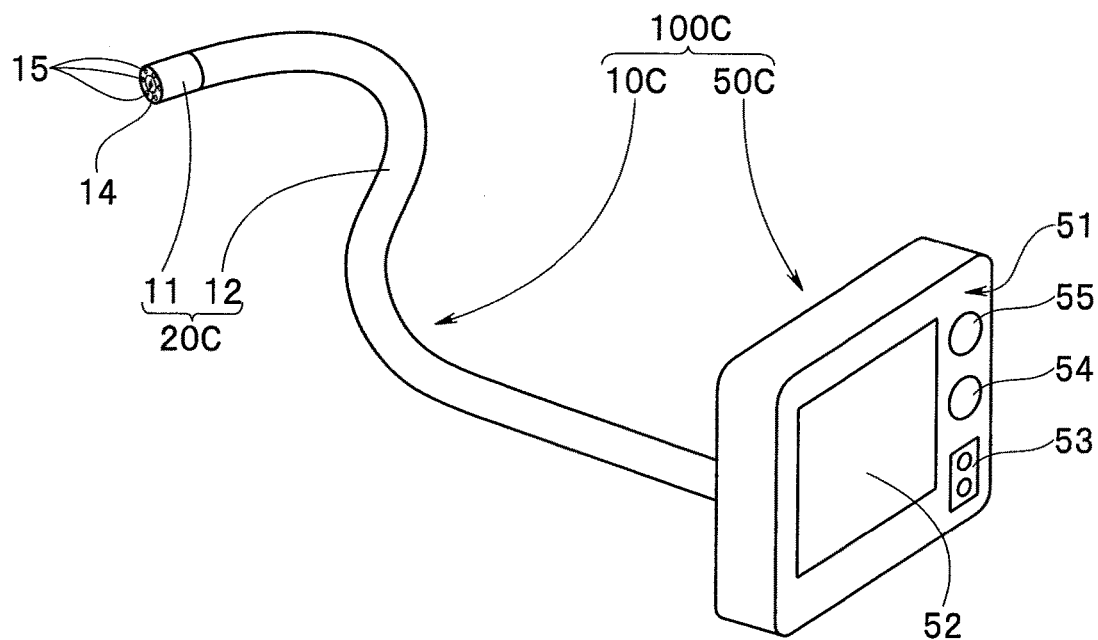
FIGS. 13 to 16 are diagrams for explaining an endoscope apparatus including an endoscope and an apparatus body according to a second embodiment of the present invention.

As shown in FIG. 13, an endoscope apparatus 100C includes the endoscope 10C and the apparatus body 50C.

The endoscope 10C according to the present embodiment includes a hard distal end portion 11 and a flexible tube portion 12 having flexibility. In other words, the endoscope 10C is a so-called insertion section 20C including the distal end portion 11 and the flexible tube portion 12. The insertion section 20C extends from the apparatus body 50 and is inserted into, for example, an engine.

An observation window 14 forming an observation optical system and illumination windows 15 forming an illumination optical system are provided, for example, on a distal end surface of the distal end portion 11. An optical image passing through the observation window 14 is formed on an image pickup surface of an image pickup device such as a CCD or a C-MOS explained later. In the figure, the observation window 14 is disposed in a center of the distal end surface and plural illumination windows 15 are arrayed around the observation window 14. Light emitting devices such as LEDs (see reference numeral 18 in FIGS. 14 and 15) are faced to the illumination windows 15.

End faces of light guide fibers for transmitting illumination light emitted from a light source lamp provided in the apparatus body 50 may be faced to the illumination windows 15.

The apparatus body 50C has a flat rectangular parallelepiped shape. The display section 52 is provided on the principal plane 51, which is one of surfaces having a largest area.

The apparatus body 50C includes various switches such as those denoted by reference numerals 53, 54, and 55 besides a power switch. The switch denoted by reference numeral 53 is, for example, a brightness switch and adjust brightness of a displayed image. The switch denoted by reference numeral 54 is, for example, an image recording switch. The switch denoted by reference numeral 55 is, for example, an image immobilizing switch.

Figure 14:
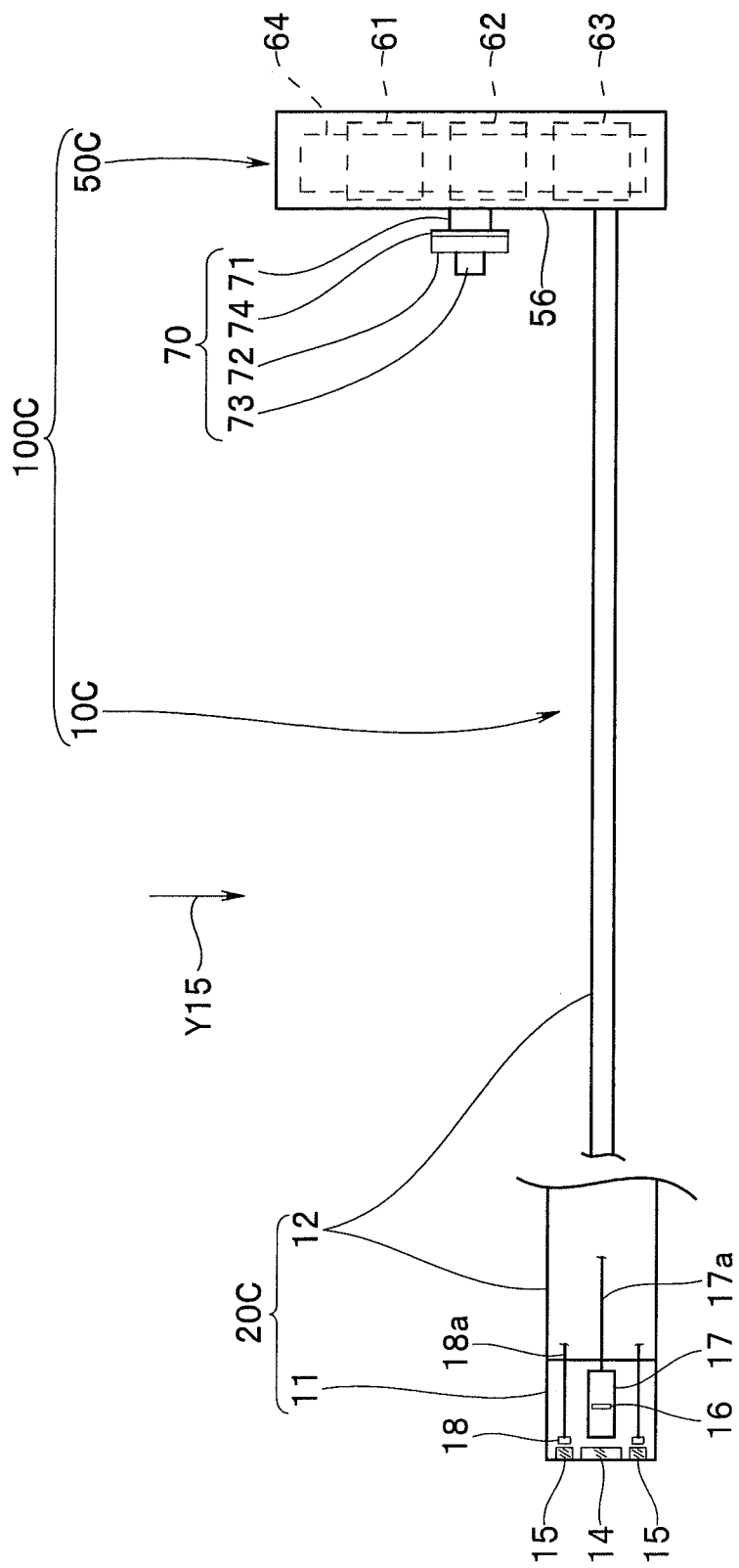
Figure 15:
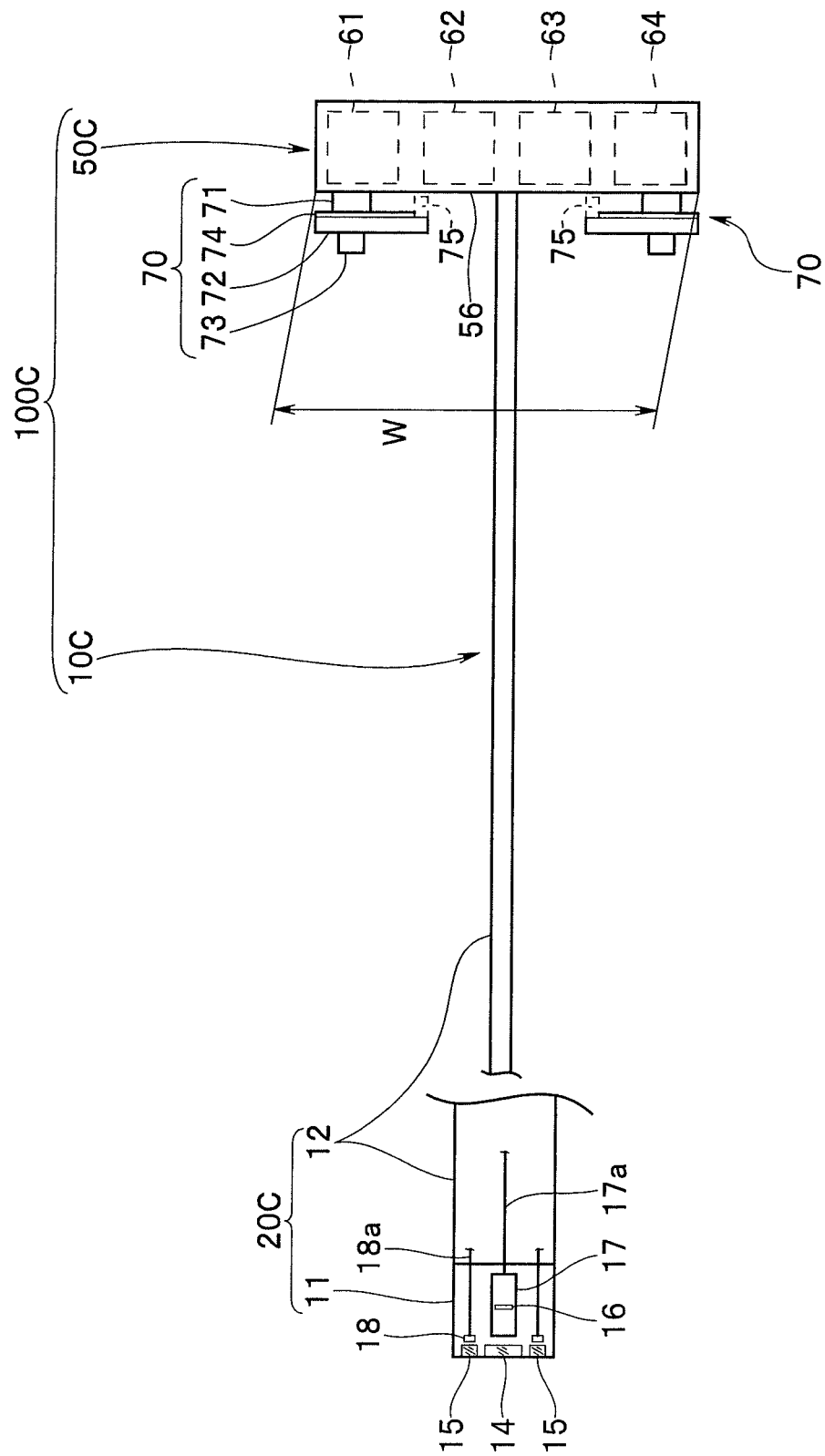

As shown in FIGS. 14 and 15, an image pickup unit 17 including an image pickup device 16 is disposed at the distal end portion 11 of the endoscope 10. A signal line 17a connected to the image pickup unit 17, power supply lines 18a for supplying electric power to the LEDs 18, and the like are inserted through the insertion section 20C.

On the other hand, the apparatus body 50C includes, on an inside thereof, an electric circuit that performs driving of the image pickup device 16, a signal processing section 61 including an image processing circuit or the like that generates a video signal from an image signal outputted from the image pickup unit 17 and outputs the video signal to a display section, a recording section 62 that records image data processed by the image processing circuit, a light source section 63 including a light adjustment circuit or the like that controls an illumination light amount, and a battery 64 or the like functioning as a power supply section that supplies necessary electric power into the endoscope 10 and the apparatus body 50C.

The apparatus body 50 includes, for example, a pair of holders 70 as holding members for holding the insertion section 20 on the holding surface 56, which is the rear surface of the principal plane 51 including the display section 52. The holders 70 include shaft sections 71 and pressing plates 72. The pressing plates 72 are pivotably attached to the shaft sections 71 by pins 73.

The shaft sections 71 also function as third regulating sections that regulate a wound-state insertion section 20D, which is held in a wound state, from widening in a radial direction. A height dimension of the shaft sections 71 is set larger than a diameter dimension of the insertion section 20C.

The pressing plates 72 are first regulating sections that regulate the wound-state insertion section 20D, which is held on the holding surface 56, from projecting in the axial direction perpendicular to the holding surface 56 and falling off. Reference numeral 74 denotes elastic members. The elastic members 74 are disposed on the holding surface 56 sides of the pressing plates 72. The elastic member 74 has predetermined elastic force and presses the insertion section 20C against the holding surface 56 to regulate movement in the gravity direction.

In this embodiment, the image pickup unit 17 is provided at the distal end portion 11. However, the image pickup unit 17 is not limited to be provided at the distal end portion 11 and may be provided, for example, on a proximal end side of the flexible tube portion 12.

Action of the endoscope apparatus 100C configured as explained above is explained.

Figure 16:
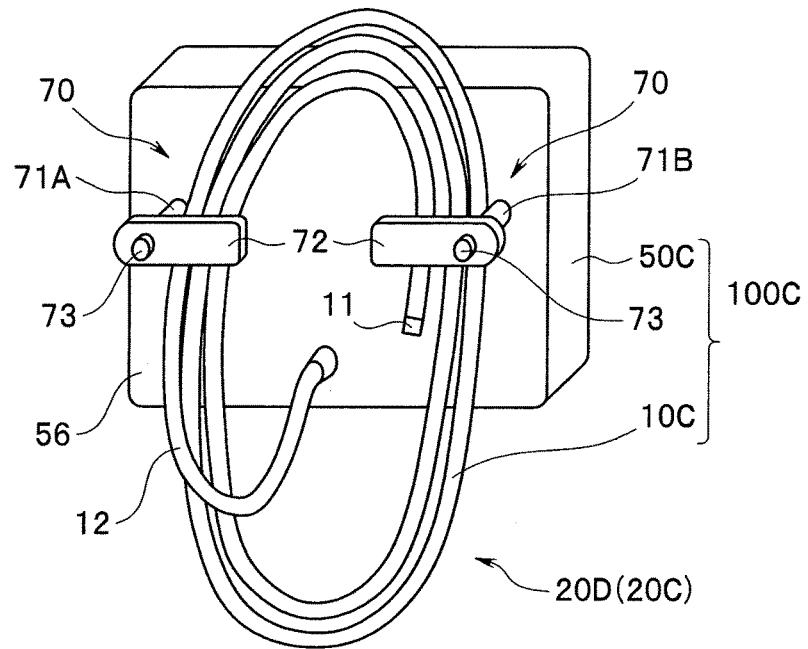

As shown in FIG. 16, the insertion section 20C, which is the endoscope 10C, is integrally attached on the holding surface 56 side of the apparatus body 50C in a wound state.

Specifically, the worker forms the wound-state insertion section 20D formed by winding the insertion section 20C and arranges this wound-state insertion section 20D between a shaft section 71A and a shaft section 71B. Thereafter, the worker rotates the pressing plates 72 with respect to the shaft sections 71 in this arrangement state and arranges the pressing plates 72 on the wound-state insertion section 20D.

Consequently, the wound-state insertion section 20D is held on the holding surface 56. In other words, an insertion section held state in which the endoscope 10C, which is the insertion section 20C, is integrally attached to the holding surface 56 of the apparatus body 50C can be obtained.

In this way, the holding members are provided on the holding surface, which is the rear surface of the principal plane on which the display section is provided. This makes it possible to integrally hold the wound-state insertion section, which is formed by winding the insertion section, on the holding surface of the apparatus body.

The holders 70 are not limited to the configuration including the shaft sections 71, the pressing plates 72, and the pins 73 shown in FIGS. 14 to 16. For example, regulating protrusions 75 indicated by broken lines in FIG. 15 may be provided on the pressing plate 72 in order to regulate the insertion section 20C from falling off in a direction of a center of the holding surface 56.

Figure 17:
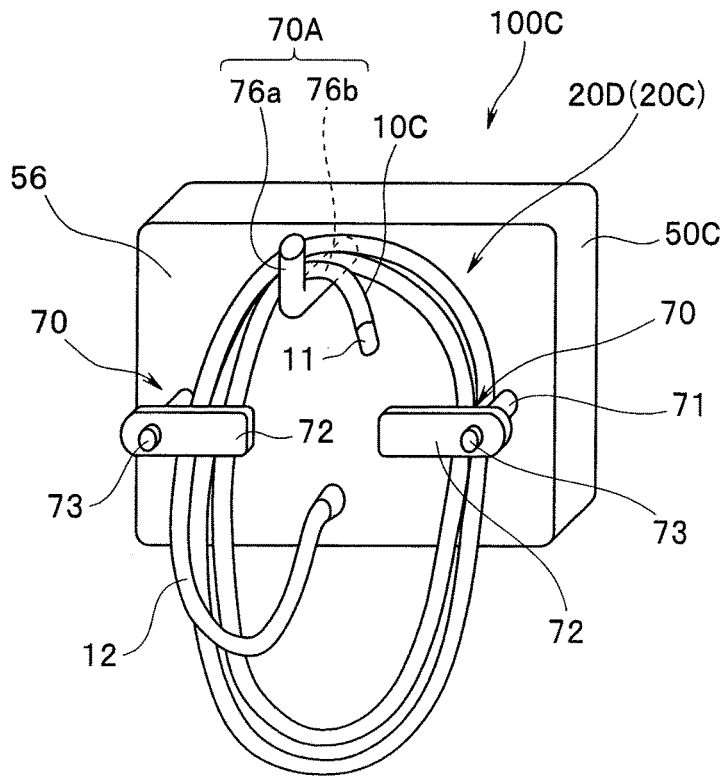
FIG. 17 is a diagram for explaining a configuration and action of another holding member provided on the holding surface of the apparatus body.

The holding members are not limited to the holders 70 including the shaft sections 71, the pressing plates 72, and the pins 73 and may be, for example, a suspender 70A shown in FIG. 17.

The suspender 70A is formed in an L shape including a protruding section 76a, which is the first regulating section, and a holding section 76b, which is the second regulating section. Therefore, in the suspender 70A, the wound-state insertion section 20D can be suspended.

The suspender 70A and the holders 70 are provided on the holding surface 56. This makes it possible to prevent falling off of the wound-state insertion section 20D from the holding surface 56 and hold the insertion section 20C on the holding surface 56 in a more stable state.

Figure 18:
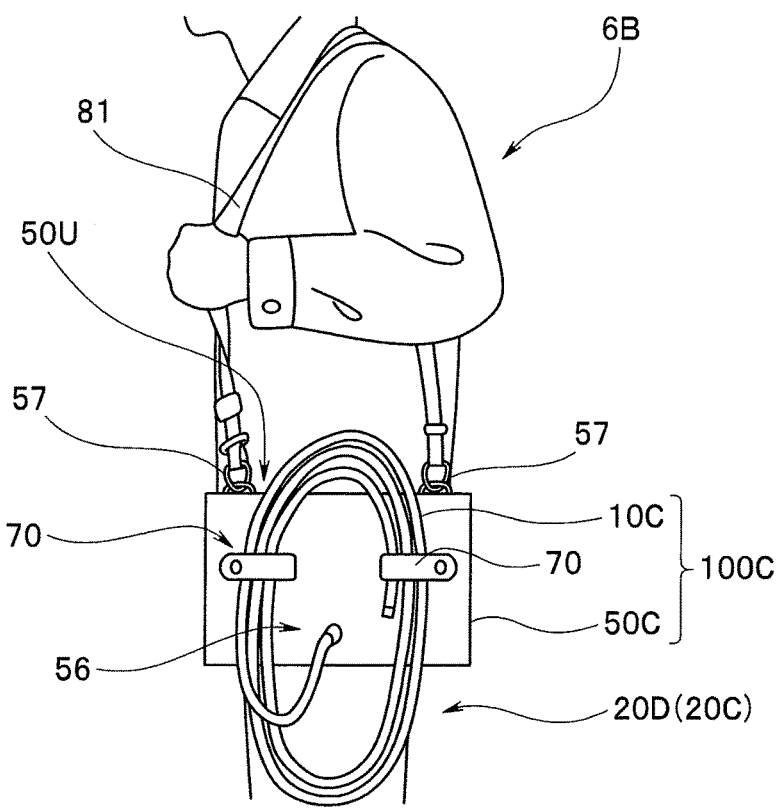
FIG. 18 is a diagram showing a state in which an operator is carrying the endoscope apparatus while slinging a belt over a shoulder.

As shown in FIG. 18, belt attaching sections 57 are provided, for example, in an upper side surface section 50U of the apparatus body 50C. Consequently, an operator 6B can easily carry the endoscope apparatus 100C, which is made compact by holding the wound-state insertion section 20D on the holding surface 56 side of the apparatus body 50C, while holding the belt 81 slung over a shoulder.

Figure 19:
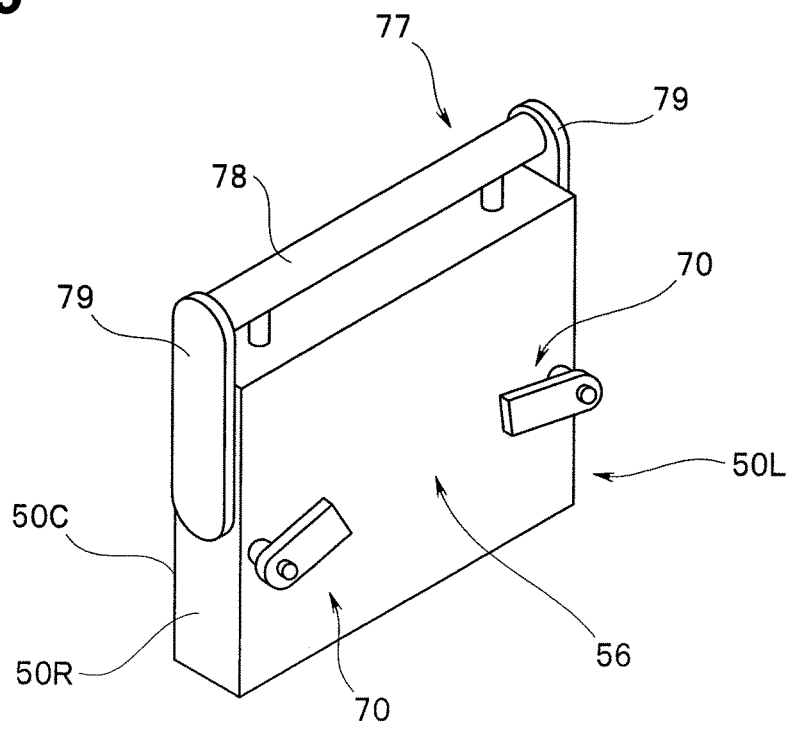
FIGS. 19 to 21 are diagrams for explaining a grip provided in the apparatus body instead of the belt.
Figure 20:
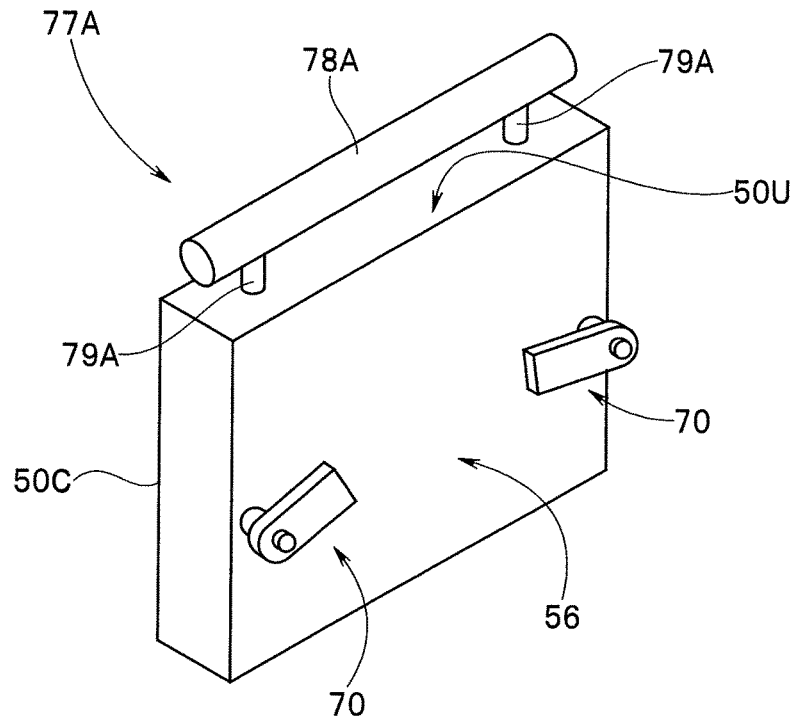
Figure 21:
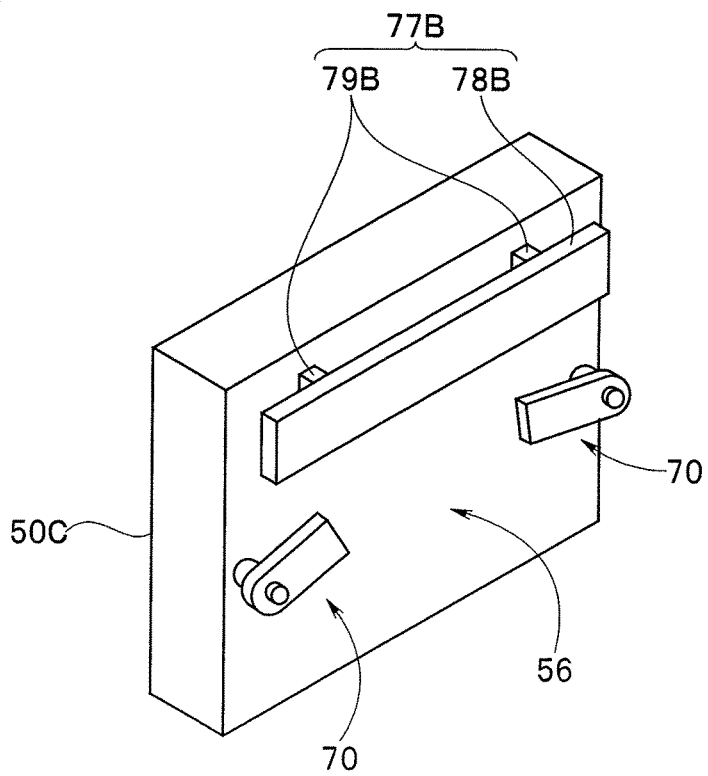

Instead of providing the belt 81 in the apparatus body 50C, grips 77, 77A, and 77B shown in FIGS. 19 to 21 may be provided.

The grip 77 shown in FIG. 19 includes a grasping bar 78 having rigidity and a pair of attaching sections 79. One end sides of the pair of attaching sections 79 are respectively fixedly set at end portions of the grasping bar 78. The other end sides of the pair of attaching sections 79 are respectively fixedly set in the left side surface section 50L and the right side surface section 50R of the apparatus body 50C.

The grip 77A shown in FIG. 20 includes a grasping bar 78A having rigidity and a pair of attaching sections 79A. One surface sides of the pair of attaching sections 79A are respectively fixedly set in the upper side surface section 50U of the apparatus body 50C. The other surface sides of the attaching sections 79A are fixedly set in predetermined section of the grasping bar 78A.

The grip 77B shown in FIG. 21 also functions as a holding member and is provided on the holding surface 56. The grip 77B includes a grasping plate 78B having rigidity and a pair of attaching sections 79B. One surface sides of the pair of attaching sections 79B are fixedly set on the holding surface 56 of the apparatus body 50C. The other surface sides of the attaching sections 79A are fixedly set in predetermined sections of the grasping bar 78A.

The grasping bar 78A and the attaching section 79A and the grasping plate 78B and the attaching section 79B also function as, at least the first regulating sections. A height dimension of the attaching sections 79A and 79B is set larger than at least a diameter dimension of the insertion section 20.

Figure 22:
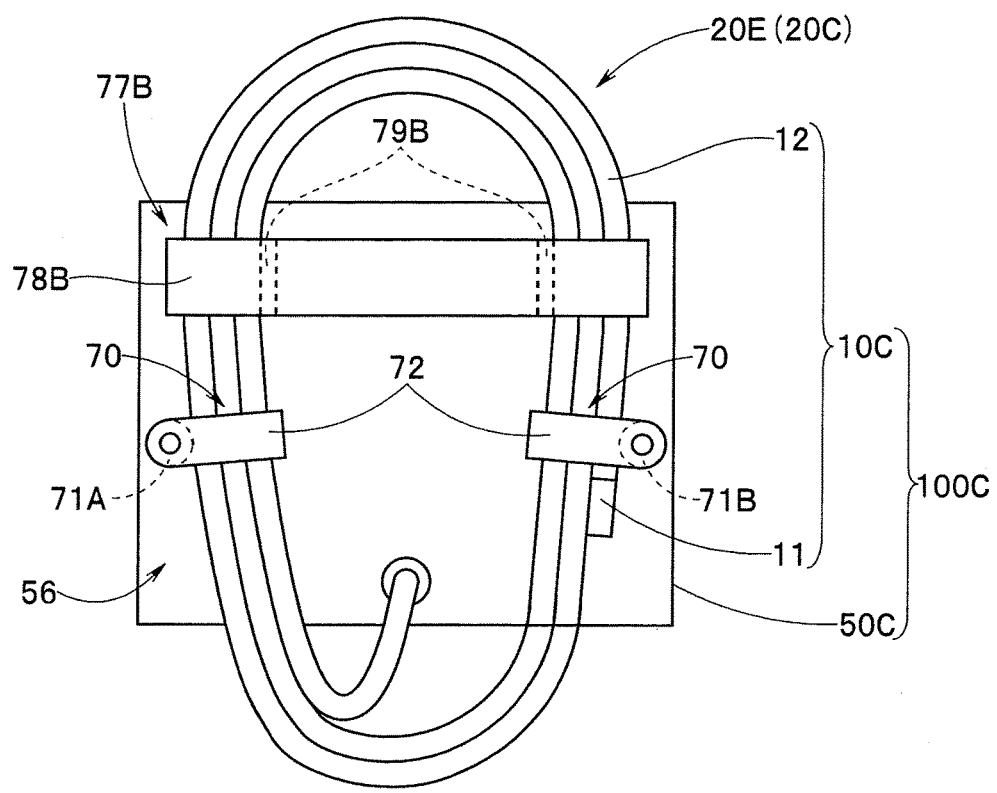
FIG. 22 is a diagram showing a state in which an insertion section is integrally held on the holding surface of apparatus body including the grip shown in FIG. 21.

As shown in FIG. 22, a wound-state insertion section 20E is arranged between the shaft section 71A and the shaft section 71B of the pair of holders 70 and in a gap between both side portions of the grasping plate 78B of the grip 77B and the holding surface 56. The pressing plates 72 are rotated with respect to the shaft sections 71 and arranged on the wound-state insertion section 20E.

Consequently, an insertion section held state in which the endoscope 10C, which is the insertion section 20C, is integrally attached to the holding surface 56 of the apparatus body 50C can be obtained.

Figure 23:
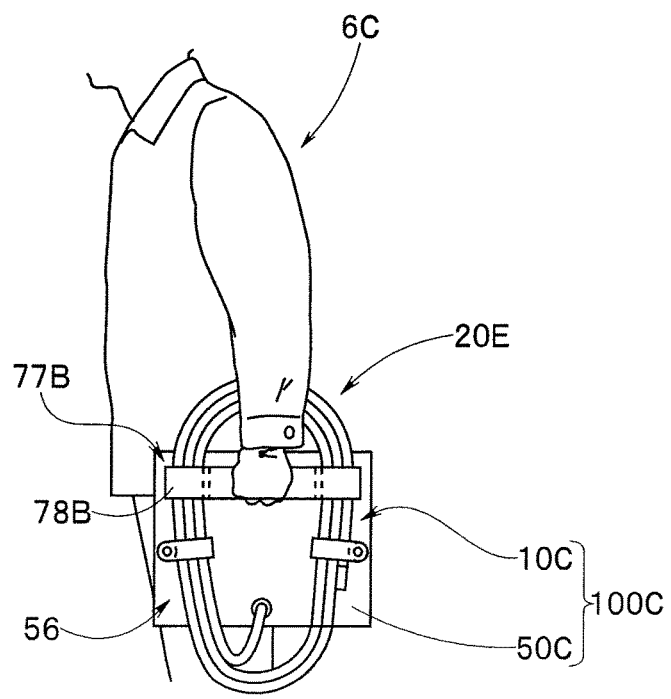
FIG. 23 is a diagram showing a state in which the operator is carrying the endoscope apparatus while gripping the grip.

As shown in FIG. 23, an operator 6C can easily carry the endoscope apparatus 100C, which is made compact by holding the wound-state insertion section 20E on the holding surface 56 side of the apparatus body 50C, by grasping the grasping plate 78B of the grip 77B provided in the apparatus body 50C.

Figure 24:
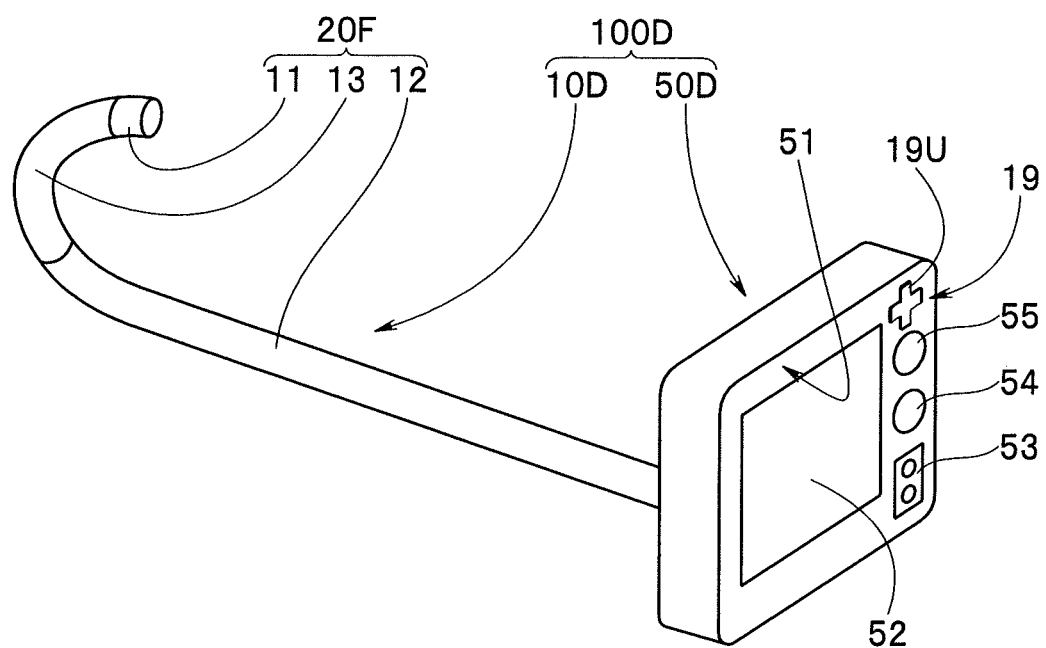
FIG. 24 is a diagram showing an endoscope apparatus including an endoscope in which a distal end portion, a bending portion, and a flexible tube portion are joined to form an insertion section and a bending operation device, which is an electric switch for causing the bending portion to perform a bending action.

In the present embodiment, the endoscope 10C, i.e., the insertion section 20C includes the distal end portion 11 and the flexible tube portion 12. However, as shown in FIG. 24, an endoscope apparatus 100D may include an endoscope 10D and an apparatus body 50D. The endoscope 10D includes an insertion section 20F in which the distal end portion 11, a bending portion 13, and the flexible tube portion 12 are joined in order from a distal end side. The bending portion 13 is configured by joining plural bending pieces (not shown) to bend, for example, up and down and to the left and right.

The apparatus body 50D includes, on the principal plane 51, an electric switch 19 as a bending operation device for bending the bending portion 13. In the present embodiment, the operator presses, for example, an upper switch 19U of the electric switch 19, whereby a not-shown bending operation wire is drawn and loosened by a not-shown driving motor and the bending portion 13 performs a bending action in an upward direction.

In the embodiments explained above, up, down, left, and right directions of the bending portions 13 and 22 coincide with up, down, left, and right directions of an endoscope image displayed on the display section 52 of the principal plane 51.

The present invention is not limited only to the embodiments explained above. Various modifications can be carried out without departing from the spirit of the invention.

What is claimed is:

1. An endoscope apparatus comprising:
    an endoscope including at least an elongated insertion section having flexibility and an image pickup device, the insertion section including, at a distal end portion, an observation window forming an observation optical system and an illumination window forming an illumination optical system and the image pickup device including an image pickup surface on which an optical image passing through the observation window is formed;
    an apparatus body incorporating a display section that displays an image picked up by the image pickup device; and
    an operation section coupled to a proximal end portion of the insertion section, and is provided with a bending operation section for operating actions of a bending portion provided to the insertion section,
    wherein the apparatus body includes a housing with multiple sides including a first side and a rear side located opposite relative to the first side of the housing, the display section is mounted to and incorporated at the first side of the apparatus housing, and on said rear side is attached the operation section which functions as a holding member that holds the insertion section on the rear side in a wound state, the operation section being attached to the rear side of the apparatus housing by an attaching and detaching mechanism section which is provided at the rear side and at the operation section and which allows the operation section to be detachably attached to the rear side;
    wherein the operation section includes a first regulating section formed by a surface of the operation section facing the rear side of the apparatus body;
    said first regulating section prevents the insertion section in the wound state from projecting in an axial direction perpendicular to the rear side;
    wherein a gap separates the first regulating section and the rear side of the apparatus housing; and
    wherein the operation section includes a holding hole through which a distal end portion of the insertion section can be inserted.

2. The endoscope apparatus according to claim 1, wherein the first regulating section is located so it faces the gap provided between a rear surface of the apparatus body and a side of the operation section where the attaching and detaching mechanism section is provided.

3. An endoscope apparatus comprising:
    an endoscope including at least an elongated insertion section having flexibility and an image pickup device, the insertion section including, at a distal end portion, an observation window forming an observation optical system and an illumination window forming an illumination optical system and the image pickup device including an image pickup surface on which an optical image passing through the observation window is formed;

an apparatus body incorporating a display section that displays an image picked up by the image pickup device; and an operation section coupled to a proximal end portion of the insertion section, and is provided with a bending operation section for operating actions of a bending portion provided to the insertion section, wherein the apparatus body includes a housing with multiple sides including a first side and a rear side located opposite relative to the first side of the housing, the display section is mounted to and incorporated at the first side of the apparatus housing, and on said rear side is attached the operation section which functions as a holding member that holds the insertion section on the rear side in a wound state, the operation section being attached to the rear side of the apparatus housing by an attaching and detaching mechanism section which is provided at the rear side and at the operation section and which allows the operation section to be detachably attached to the rear side;

wherein the operation section includes a second regulating section which is a protruding section of the operation section which is protruded on a side of the operating section;

said second regulating section regulates movement in a gravity direction of the insertion section in the wound state, while held on a rear surface of the operation section;

wherein said second regulating section faces a gap provided between the rear side of the apparatus housing and the operation section; and wherein the operation section includes a holding hole through which the distal end portion of the insertion section can be inserted.

4. The endoscope apparatus according to claim 3, wherein the second regulating section is arranged so it faces the gap provided between a rear surface of the apparatus body and a side of the operation section where the attaching and detaching mechanism section is provided.

5. An endoscope apparatus according to claim 3, wherein the second regulating section includes the attaching and detaching mechanism section.

\* \* \* \* \*